(12) United States Patent
Shih

(10) Patent No.: US 8,079,873 B2
(45) Date of Patent: Dec. 20, 2011

(54) LVDS CONNECTOR

(75) Inventor: Hsien-Kuang Shih, Chang Hwa (TW)

(73) Assignee: K.S. Terminals Inc., Chang Hwa County (TW)

( * ) Notice: Subject to any disclaimer, the term of this patent is extended or adjusted under 35 U.S.C. 154(b) by 204 days.

(21) Appl. No.: 12/510,318

(22) Filed: Jul. 28, 2009

(65) Prior Publication Data

US 2010/0255725 A1    Oct. 7, 2010

(51) Int. Cl.
*H01R 13/648* (2006.01)

(52) U.S. Cl. .................................. 439/607.28

(58) Field of Classification Search ............. 439/607.01, 439/607.04, 607.28, 95
See application file for complete search history.

(56) References Cited

U.S. PATENT DOCUMENTS 6,890,193 B2 *   5/2005   Kimura et al. ................ 439/108

FOREIGN PATENT DOCUMENTS

TW              200423491        11/2004

\* cited by examiner

*Primary Examiner* — Vanessa Girardi

(74) *Attorney, Agent, or Firm* — Ming Chow; Sinorica, LLC

(57) ABSTRACT

A low-voltage differential signaling (LVDS) connector includes an insulating body, a plurality of conductive terminals, and a conductive housing. The insulating body has a first opening, a second opening, and a central receiving area between the first and second openings. The central receiving area is provided with receiving grooves which are arranged along a first direction and configured for receiving the conductive terminals. The LVDS connector is characterized by a pair of conductive connecting devices, each having a first contact portion. Moreover, the conductive housing covers an exterior portion of the insulating body and is provided with a pair of second contact portions. The second contact portions are electrically connected to the first contact portions of the conductive connecting devices.

7 Claims, 3 Drawing Sheets

US 8,079,873 B2

LVDS CONNECTOR

BACKGROUND OF THE INVENTION

1. Technical Field

The present invention relates to electric connectors and, more particularly, to a low-voltage differential signaling (LVDS) connector.

2. Description of Related Art

Nowadays, with the prevalence of consumer electronics, it is commonplace to transfer and process all kinds of data through electronic products. Generally, electronic products or electronic components must be connected via electric connectors in order to implement two-way data transfer. Low-voltage differential signaling (LVDS) connectors are among the most popular electric connectors of today and are usually used in electronic devices to transmit high-voltage and low-voltage signals. However, regardless of the type, electric connectors in operation are subject to signal interference caused by external static electricity, electromagnetic waves, or noise. To prevent such interference, it is common practice to cover an exterior portion of an electric connector with a shielding housing made of a metal material, wherein the shielding housing is further connected to a grounding circuit or to a connecting wire of a circuit board so as to provide a grounding effect, thereby protecting the electric connector against interference by external noise, electromagnetic waves, or static electricity during operation.

While signal interference can be reduced by grounding the metal housing of an electric connector, the grounding and electromagnetic shielding effects provided by the prior art leave much to be desired.

BRIEF SUMMARY OF THE INVENTION

In order to overcome the aforesaid shortcomings of the prior art, the present invention provides an LVDS connector including an insulating body, a plurality of conductive terminals, and a conductive housing. The insulating body has a first opening, a second opening, and a central receiving area provided between the first opening and the second opening. The central receiving area is provided with a plurality of receiving grooves which are arranged along a first direction and are configured for receiving the conductive terminals. Each of the receiving grooves extends in a second direction perpendicular to the first direction. The conductive terminals further include a specific number of ground terminals. The LVDS connector is characterized by further including a pair of conductive connecting devices provided respectively at two ends of the central receiving area of the insulating body, wherein each of the conductive connecting devices has a first contact portion. The LVDS connecter is also characterized in that the conductive housing covers an exterior portion of the insulating body, and the conductive housing is provided with a pair of second contact portions, wherein the second contact portions are adjacent to the first opening of the insulating body. The second contact portions are configured for electrically connecting with the first contact portions of the conductive connecting devices.

Therefore, the primary objective of the present invention is to provide an LVDS connector, wherein the LVDS connector includes conductive connecting devices whose first contact portions are connected with second contact portions of a conductive housing, thereby furnishing the LVDS connector with an enhanced grounding effect.

Another objective of the present invention is to provide an LVDS connector, wherein the LVDS connector includes conductive connecting devices whose first contact portions are connected with second contact portions of a conductive housing, thereby furnishing the LVDS connector with an enhanced electromagnetic shielding effect.

BRIEF DESCRIPTION OF THE SEVERAL VIEWS OF THE DRAWINGS

The invention as well as a preferred mode of use, further objectives, and advantages thereof will be best understood by referring to the following detailed description of an illustrative embodiment in conjunction with the accompanying drawings, wherein.

DETAILED DESCRIPTION OF THE INVENTION

The present invention provides a low-voltage differential signaling (LVDS) connector, wherein the principles of signal transmission and grounding are well known to a person of ordinary skill in the art and therefore will not be detailed herein. Besides, it is to be understood that the drawings referred to in the following description are intended to demonstrate features of the present invention only schematically, so the drawings are not necessarily drawn to scale.

Figure 1:
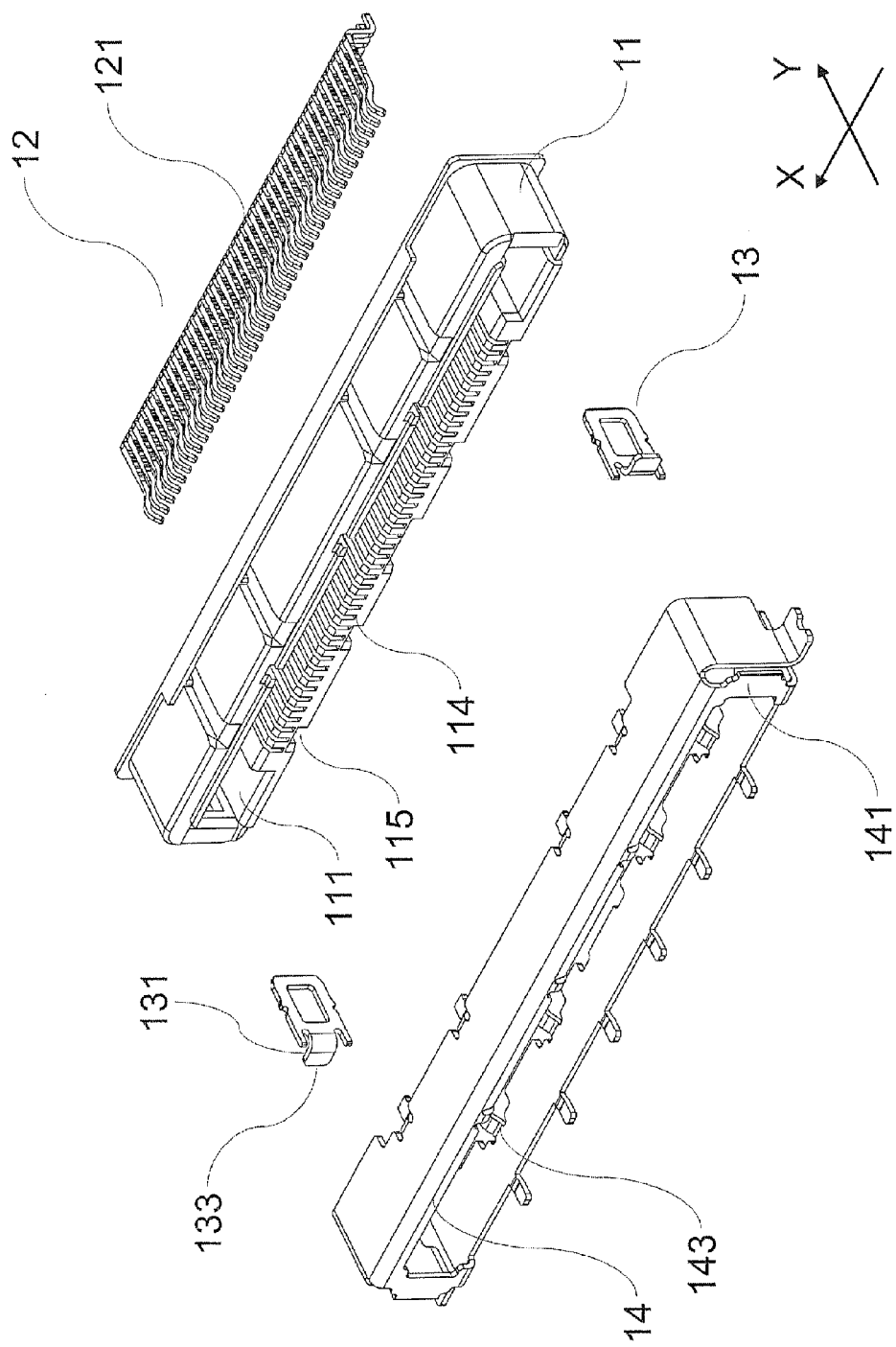
FIG. 1 is an exploded perspective view of an LVDS connector according to a preferred embodiment of the present invention.
Figure 2:
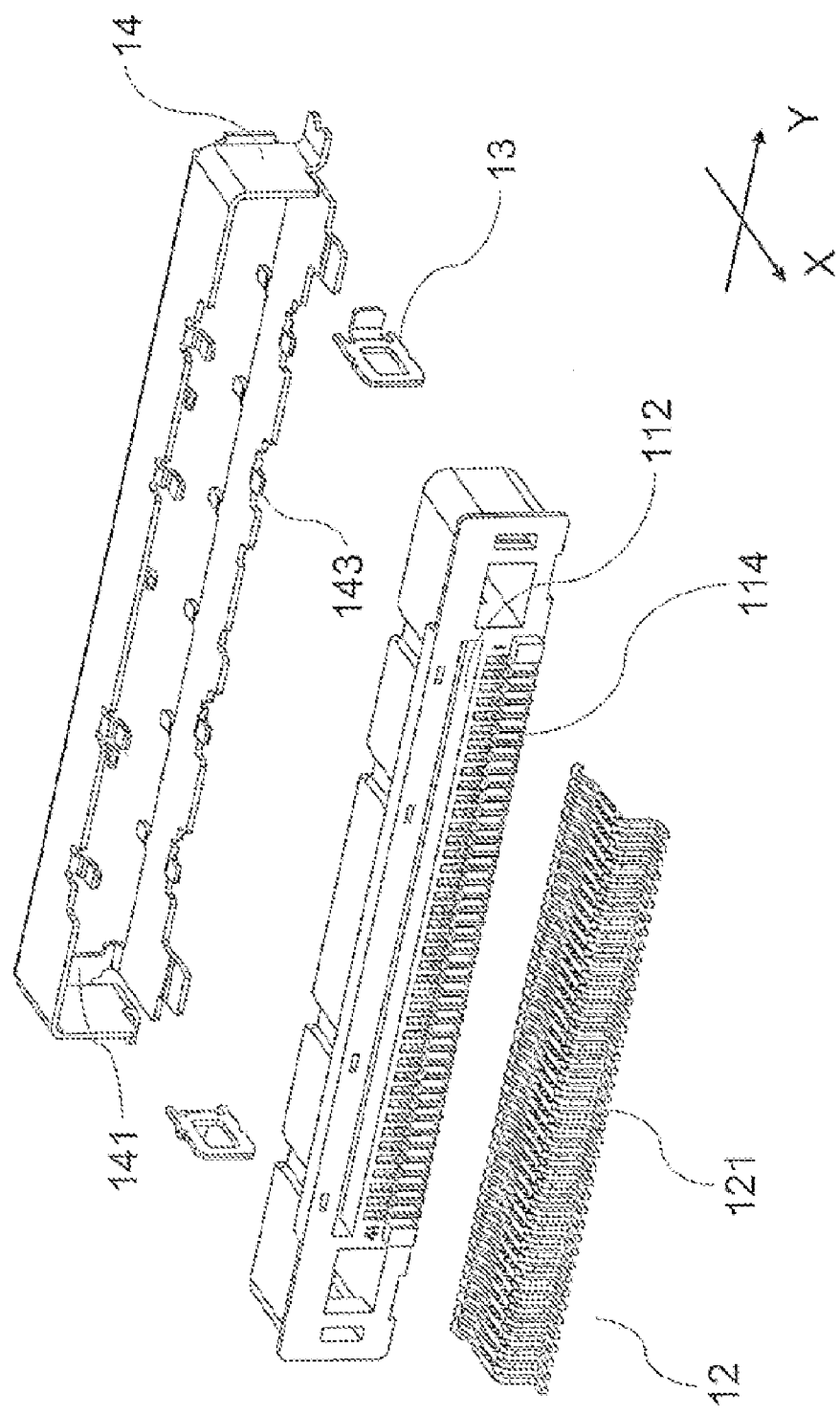
FIG. 2 is an exploded perspective view of the LVDS connector according to the preferred embodiment of the present invention when viewed from another angle.
Figure 3:
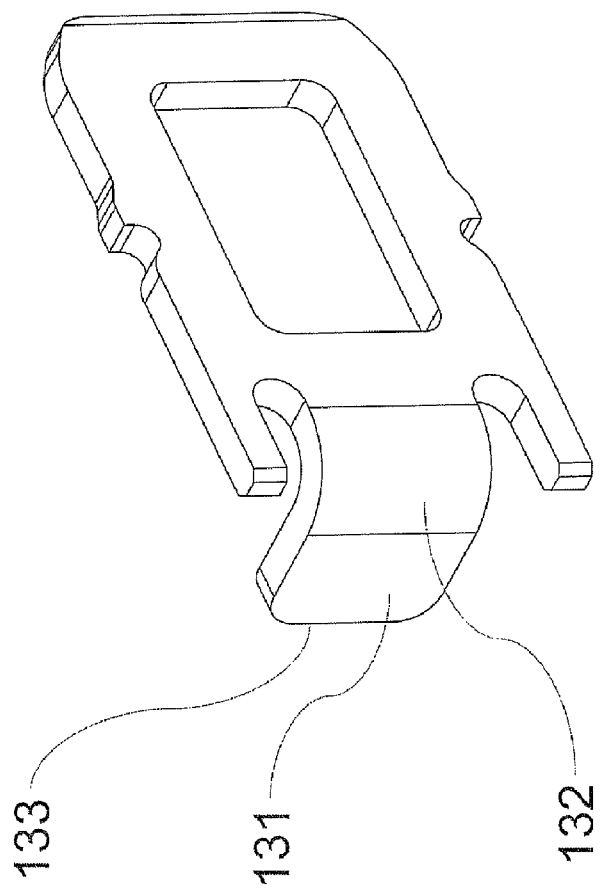
FIG. 3 is a perspective view of a conductive connecting device of the LVDS connector according to the present invention.

Referring to FIG. 1, FIG. 2 and FIG. 3, an LVDS connector according to a preferred embodiment of the present invention includes an insulating body 11, a plurality of conductive terminals 12, and a conductive housing 14. The insulating body 11 has a first opening 111, a second opening 112, and a central receiving area 113 disposed between the first opening 111 and the second opening 112. The central receiving area 113 is provided with a plurality of receiving grooves 114 which are arranged along a first direction X and are configured for receiving the conductive terminals 12. Each of the receiving grooves 114 extends in a second direction Y. The second direction Y is perpendicular to the first direction X. The conductive terminals 12 further include a specific number of ground terminals 121. The LVDS connector is characterized by further including a pair of conductive connecting devices 13 provided at two ends of the central receiving area 113 of the insulating body 11, respectively, wherein each of the conductive connecting devices 13 has a first contact portion 131. The LVDS connector is further characterized in that the conductive housing 14 covers an exterior portion of the insulating body 11 and is provided with a pair of second contact portions 141. The second contact portions 141 are adjacent to the first opening 111 of the insulating body 11. The second contact portions 141 are configured for electrically connecting with the first contact portions 131 of the conductive connecting devices 13. Thus, the conductive housing 14 is connected to the first contact portions 131 via the second contact portions 141. In consequence, the LVDS connector is enhanced in both its grounding effect and electromagnetic shielding effect.

In the foregoing embodiment, the first contact portion 131 of each of the conductive connecting devices 13 is further bent outward to form a bent portion 132. Moreover, the first contact portion 131 forms a resilient arm 133 extending in the first direction X and having a pivot point defined by the bent portion 132.

Further, in the foregoing embodiment, the pair of second contact portions 141 of the conductive housing 14 are a pair of stop plates provided at two ends of the conductive housing 14 along the first direction X, respectively, and configured for pressing against the resilient arms 133 of the conductive connecting devices 13 so as to form electrical connection. As the resilient arms 133 extend along the first direction X, the area of contact between the conductive connecting devices 13 and the conductive housing 14 is increased, thus providing enhanced electrical connection.

Additionally, in the foregoing embodiment, the insulating body 11 is further provided with a plurality of engaging slots 115. The engaging slots 115, which are provided at the exterior portion of the insulating body 11, are arranged along the first direction X and extend in the second direction Y. Besides, the conductive housing 14 further includes a plurality of engaging blocks 143. The engaging blocks 143 also are arranged along the first direction X and extend in the second direction Y. Moreover, the engaging blocks 143 correspond in position to the engaging slots 115 of the insulating body 11 and are engageable with the engaging slots 115, thus allowing the insulating body 11 to be inserted into the conductive housing 14 along the second direction Y, with the first opening 111 facing the conductive housing 14.

The present invention is herein described by reference to the preferred embodiment. It is understood that the embodiment is not intended to limit the scope of the present invention. Furthermore, as the contents disclosed herein should be readily understood and can be implemented by a person skilled in the art, all equivalent changes or modifications which do not depart from the spirit of the present invention should be encompassed by the appended claims.

What is claimed is:

1. A low-voltage differential signaling (LVDS) connector, comprising an insulating body, a plurality of conductive terminals, and a conductive housing, the insulating body having a first opening, a second opening, and a central receiving area between the first opening and the second opening, the central receiving area being provided with a plurality of receiving grooves which are arranged along a first direction and are configured for receiving the conductive terminals, each said receiving groove extending in a second direction perpendicular to the first direction, the conductive terminals further comprising a specific number of ground terminals, the LVDS connecter being characterized by:

the LVDS connector further comprising a pair of conductive connecting devices provided at two ends of the central receiving area of the insulating body, respectively, wherein each said conductive connecting device has a first contact portion; and the conductive housing covering an exterior portion of the insulating body, the conductive housing being provided with a pair of second contact portions adjacent to the first opening of the insulating body, wherein the pair of second contact portions are configured for electrically connecting with the first contact portions of the conductive connecting devices;

wherein:

each said conductive connecting device further comprises a bent portion, and the first contact portion is bent outward from the bent portion; and each said first contact portion is a resilient arm having a pivot point defined by the bent portion such that the resilient arm extends in the first direction.

2. The LVDS connector of claim 1, wherein the conductive housing is fitted around the exterior portion of the insulating body along the second direction, with the conductive housing facing the first opening of the insulating body.

3. The LVDS connector of claim 1, wherein the pair of second contact portions of the conductive housing are a pair of stop plates, each said stop plate being configured for pressing against the resilient arm of a corresponding said conductive connecting device so as to form electrical connection.

4. The LVDS connector of claim 3, wherein the pair of second contact portions are provided at two ends of the conductive housing along the first direction, respectively.

5. The LVDS connector of claim 1, wherein the insulating body is provided with a plurality of engaging slots arranged along the first direction and extending in the second direction.

6. The LVDS connector of claim 5, wherein the engaging slots are provided at the exterior portion of the insulating body.

7. The LVDS connector of claim 5, wherein the conductive housing is provided with a plurality of engaging blocks arranged along the first direction and extending in the second direction, the engaging blocks being engaged with the engaging slots of the insulating body.

* * * * *